United States Patent

Bruder et al.

(10) Patent No.: US 6,411,671 B2
(45) Date of Patent: Jun. 25, 2002

(54) METHOD FOR REDUCING LINE ARTIFACTS IN A CT IMAGE AND DEVICE FOR IMPLEMENTING THE METHOD

(75) Inventors: Herbert Bruder, Höchstadt; Thomas Flohr, Uehlfeld; Karl Stierstorfer, Erlangen; Thomas Von Der Haar, Nürnberg, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/797,330

(22) Filed: Mar. 1, 2001

(30) Foreign Application Priority Data

Mar. 1, 2000 (DE) .......................................... 100 09 746

(51) Int. Cl.[7] .................................................. A61B 6/00
(52) U.S. Cl. ............................... 378/4; 378/15; 378/19; 364/413; 364/414
(58) Field of Search ............................ 378/4, 19, 901, 378/21–22, 98, 15; 364/413, 414

(56) References Cited

U.S. PATENT DOCUMENTS

| 4,670,840 | A | * | 6/1987 | Freundlich | 378/4 |
|---|---|---|---|---|---|
| 5,025,463 | A | * | 6/1991 | Saito et al. | 378/19 |
| 5,960,056 | A | * | 9/1999 | Lai | 378/15 |
| 6,047,039 | A | * | 4/2000 | Flohr | 378/4 |
| 6,115,445 | A | * | 9/2000 | Lai | 378/4 |
| 6,178,220 | B1 | * | 1/2001 | Freundlich et al. | 378/15 |

* cited by examiner

Primary Examiner—Robert H. Kim
Assistant Examiner—George Wang
(74) Attorney, Agent, or Firm—Schiff Hardin & Waite (57) ABSTRACT

In a method and apparatus for reducing line artifacts in a CT image $D_1$, which is acquired during a scan by a CT device with a detector system having a number of proper detector channels and at least one defective detector channel, the image $M_1$ is obtained first by a median filtering the image $D_1$, which contains a circle artifact on a circle $K_1$. A difference value image $F_1 = D_1 - M_1$ is then produced. Filtering then is carried out in each picture element of the image $F_1$ in the direction of the tangents $t^1_1$ and $t^2_1$ to the circle $K_1$ extending through the respective picture element in order to produce two resulting images $G^1_1$ and $G^2_1$. A correction image $D_2$ is subsequently produced by subtracting the resulting images $G^1_1$ and $G^2_1$ from $D_1$.

40 Claims, 8 Drawing Sheets

METHOD FOR REDUCING LINE ARTIFACTS IN A CT IMAGE AND DEVICE FOR IMPLEMENTING THE METHOD

BACKGROUND OF THE INVENTION

1. Field of the Invention

The present invention is directed to a method and apparatus for reducing line artifacts in a CT image, wherein the CT image is produced by scanning with an X-ray source which is rotatable around an examination subject, with X-rays from the X-ray source, after being attenuated by an examination subject, being incident on a detector system.

2. Description of the Prior Art

CT devices are known which have an X-ray source, e.g. an X-ray tube, which direct a collimated, pyramid-shaped X-ray bundle through the examination subject, e.g. a patient, onto a detector system that is composed of a number of detector channels. Each detector channel has at least one detector element and one associated electronic element for reading out and amplifying the signal that is generated in the detector element as a result of the incident radiation. A number of detector elements can be allocated to one electronic element. The X-ray source and, depending on the construction of the CT device, the detector system as well are attached to a gantry that rotates around the examination subject. A support device for the examination subject can be displaced along the system axis relative to the gantry. The position along the system axis at which the X-ray bundle penetrates the examination subject, and the angle, under which the X-ray bundle penetrates the examination subject, are continuously modified as a result of the displacement and the rotation of the gantry. Each detector element of the detector system struck by the radiation produces a signal representing a measure of the overall transparency of the examination subject for the radiation proceeding from the X-ray source to the detector system. The set of output signals of the detector element, of the detector system, which is acquired for a specific position of the X-ray source, is referred to as a projection. A scan is composed of a set of projections, which are acquired at different positions of the gantry and/or at different positions of the support device. The CT device picks up a number of projections during a scan in order to be able to construct a two-dimensional tomogram of a slice of the examination subject. A number of slices can be picked up at the same time by a detector system that is composed of an array having a number of rows and columns of detector elements. Such planar-like detector systems, however, frequently contain detector channels which do not supply proper data. It may be that detector system contains faulty detector channels already after the production process, for example as a result of defects in fabrication caused by the high integration density of the electronic elements. Defects of individual detector channels also may arise during the operation of the CT device. Such defects cause circular structures in the acquired CT images, these circular structures being referred to as circle artifacts. Techniques referred to as "ring-balancing" methods are known from the literature for the purpose of attempting to correct or prevent such artifacts in CT images. Such methods are disclosed in U.S. Pat. No. 4,670,840 and in German OS 198 35 451 (corresponding to U.S. Pat. No. 6,047,039), for example.

A disadvantage of such known methods is that they insufficiently eliminate artifacts which arise in a CT device having a defective detector channel.

SUMMARY OF THE INVENTION

An object of the present invention is to provide a method for reducing artifacts in a CT image, so that the obtainable image quality is improved in a CT device having at least one defective detector channel. It is also an object of the invention to provide a CT device for implementing the method.

The above object is achieved in accordance with the principles of the present invention in a method for reducing line artifacts in a CT image $D_1$, as well as in an apparatus for implementing the method, wherein the image has been subjected to interpolated filtering for preventing or correcting faulty values of picture elements represented in a circle $K_1$, and wherein the following steps are implemented. The picture elements of the CT image $D_1$ are subjected to a median filtering, orthogonal to the straight line extending through the respective picture element and the center of the circle $K_1$, for producing an image $M_1$. A difference value image $F_1$ is generated by subtracting the image $M_1$ from the CT image $D_1$. Two resulting images $G^1_1$ and $G^2_1$ are produced by filtering the picture elements of the difference value image $F_1$ in the respective directions of tangents $t^1_1$ and $t^2_1$ to the circle $K_1$ extending through the respective picture element. Filtering is conducted along $t^1_1$ to produce the resulting image $G^1_1$ and is conducted along $t^2_1$ for producing the resulting image $G^2_1$. A correction image $D_2$ is then obtained by subtracting both of the resulting images $G^1_1$ and $G^2_1$ from the image $D_1$.

Defective detector channels of a detector system lead to faulty values for picture elements, which appear as a circle in a CT image acquired by the detector system. Such image errors therefore are referred to as circle artifacts. Defective detector channels are not only ones that fail to supply an output signal as a result of the defect, but also are channels with a measuring accuracy that exceeds a specific tolerance value. Various methods are known for correcting or preventing circle artifacts, as noted above. These methods are carried out on the measurement data or on the image data and are primarily based on interpolated filtering, and achieve a noticeable weakening of the circle artifacts in the acquired CT images. Such known methods have the disadvantage, however, that line-like image errors frequently arise in the resulting CT images after such a method has been implemented. These image errors are referred to as line artifacts. They increasingly occur in association with large signal unsteadiness caused by high-contrast areas of an examination subject. The inventive method is particularly advantageous for eliminating such line artifacts, which occur after circle artifacts have been eliminated and which appear as tangents to the circles in the CT image. The size and position data of the circles of the circle artifacts caused by the defective detector channels are assumed to be known. It is sufficient to know the position of the circle center, which is the same for all circles, and the radii of the circles.

The elimination of the line artifacts is initially described for the case of a single defective detector channel. The faulty values of picture elements caused by the defective detector channel are situated on a circle $K_1$. These faulty values are corrected by a known ring-balancing method on the measuring data or on the image data. Line artifacts, which appear as tangents to the circle $K_1$, arise in the resulting CT image $D_1$. For producing an image $M_1$, a median filtering is carried out for each picture element of the CT image $D_1$ situated outside of the circle $K_1$, orthogonally to the straight line extending through the respective picture element and the center of the circle $K_1$. The width of the median filtering can be modifiable. This width should be selected wider than the expected line width of the line artifacts. A median filter of the width 5 has proven to be beneficial. The sampling distance $A_1$ must be selected dependent on the convolution kernel used for the reconstruction. Ideally, the image $M_1$ no longer contains line artifacts.

A difference value image $F_1=D_1-M_1$ is generated by subtracting the image $M_1$ from the CT image $D_1$. For producing two resulting images $G^1_1$ and $G^2_1$, a filtering is carried out in each picture element of the difference value image $F_1$ in the respective directions of the tangents $t^1_1$ and $t^2_1$ to the circle $K_1$ extending through the picture element in question, i.e., the filtering is carried out along $t^1_1$ for the resulting image $G^1_1$ and the filtering is carried out along $t^2_1$ for the resulting image $G^2_1$. This step is to eliminate, for the most part, the image pixel noise difference value in the image $F_1$ for the most part. Furthermore, the line artifacts that are present in the error image $F_1$ are emphasized in the result images. It is necessary to calculate two result images $G^1_1$ and $G^2_1$, since there are two possible tangent directions to the circle $K_1$ per picture element. The thus-determined resulting images $G^1_1$ and $G^2_1$ are subtracted from $D_1$ and the correction image $D_2$ is obtained, which ideally no longer contains line artifacts generated by the defective channel.

The correction image $D_2$ serves as basis image for correcting the line artifacts caused by other detector channels if the detector system contains further defective detector channels. In general, the correction image $D_i$ serves as a basis image for correcting line artifacts caused by the i-th defective detector channel. Since the image $M_1$ has been calculated in relation to the center of the circle that is valid for all circles $k_i$, the difference value image $F_1$ can still be used in the following. For producing the result images $G^1_i$ and $G^2_i$, a filtering is carried out in each picture element of the difference value image $F_1$ situated outside of the circle $K_i$ in the direction of the tangents $D^1_i$ and $D^2_i$ to the circle $K_i$, i.e., the filtering is carried out along $D^1_i$ for the resulting image $G^1_i$ and the filtering is carried out along $D^2_i$ for the resulting image $G^2_i$. The correction image $D_{i+1}=D_i-G^1_i-G^2_i$ is determined by subtracting the resulting images $G^1_i$ and $G^2_i$ from $D_i$. This procedure is repeated until the line artifacts of all defective detector channels are eliminated.

The above-described method is relatively time-consuming as a result of the serial processing of the line artifacts caused by the defective detector channels. Parallel processing of the image errors caused by the different defective detector channels is preferable for processing the data faster. Accordingly, a further embodiment of the inventive method proceeds as described above until the calculation of the difference value image $F_1$. The resulting images $G^1_i$ and $G^2_i$ are calculated in this manner for all defective detector channels. In contrast to the initially described embodiment, different correction images are not consecutively determined, which respectively serve as an image for calculating the next correction images, but instead all resulting images $G^1_i$ and $G^2_i$ are subtracted from $D_1$. The correction image $D_2$ results. The defective detector channels should have a minimum distance (spacing) of ten detector channels as a condition for this parallel processing.

The aforementioned median filtering for producing an image $M_1$, in each picture element of the initial CT image, takes place orthogonally to the straight line extending through the picture element in question and the center of the circle $K_i$. This calculation represents an approximation, and it is an advantage of the inventive method that it must be carried out only once for each picture element even given a number of defective detector channels. Better results are obtained, however, by the median filtering orthogonal to the tangents to the circles $K_i$. This makes it necessary to carry out the pixel-oriented median filtering anew for each defective detector channel, with an associated high computing outlay. Given a single defective detector channel and the faulty values of picture elements on a circle $K_1$ caused as a result thereof, the correction includes the following steps:

carrying out an interpolated filtering of the artifact-containing CT image, thereby leading to the CT image $D_1$, in order to avoid or to correct faulty values of picture elements on the circle $K_1$, carrying out a median filtering in each picture element of the CT image $D_1$ situated outside of the circle $K_1$, orthogonal to the tangents to the circle $K_1$ extending through the respective picture element, for producing an image $M_1$, generating a difference value image $F_1=D_1-M_1$ by subtracting the image $M_1$ from the CT image $D_1$, carrying out a filtering in each picture element of the difference value image $F_1$ situated outside of the circle $K_1$ in the direction of the tangents $t^1_1$ and $t^2_1$ to the circle $K_1$ extending through the respective picture element in order to produce two resulting images $G^1_1$ and $G^2_1$, with the filtering being carried out along $t^1_1$ for the resulting image $G^1_1$ and the filtering is carried out along $t^2_1$ for the resulting image $G^2_1$.

determining the correction image $D_2=D_1-G^1_1-G^2_1$ by subtracting the resulting images $G^1_1$ and $G^2_1$ are from $D_1$.

If a number of defective detector channels are present, the following applies for processing the i-th defective detector channel:

a median filtering is carried out in each picture element of the CT image $D_i$, orthogonal to the tangents to the circle $K_i$ extending through the respective picture element, for producing an image $M_i$, a difference value image $F_i=D_i-M_i$ is produced by subtracting the image $M_i$ from the correction image $D_i$, a filtering is carried out in each picture element of the difference value image $F_1$ situated outside of the circle $K_1$ in the direction of the tangents $t^1_i$ and $t^2_i$ to the circle $K_i$ extending through the respective picture element in order to produce two resulting images $G^1_i$ and $G^2_i$, with the filtering being carried out along $t^1_i$ for the resulting image $G^1_i$ and the filtering being carried out along $t^2_i$ for the resulting image $G^2_i$.

the correction image $D_{i+1}=D_i-G^1_i-G^2_i$ is determined by subtracting the resulting images $G^1_i$ and $G^2_i$ from $D_i$.

These steps are repeated until all image errors caused by the different defective detector channels are processed.

In a further version of the invention, a running averaging serves as the filtering for producing the resulting images $G^1_i$ and $G^2_i$. In another version of the invention, a sum operator is implemented as the filtering for producing the resulting images $G^1_i$ and $G^2_i$. A combination of these two versions also can be employed, wherein a running averaging and a sum operator are simultaneously employed for filtering.

At the beginning of each of the aforementioned embodiments, the values of the CT image $D_1$ are preferably limited to a range 1000 HU $(H_2O)\pm\Delta$. This limitation is expedient for examining soft-tissue parts, in which disturbances caused by defective detector channels are particularly apparent in the image.

The intensity of the noise signal in the resulting images $G^1_i$ and $G^2_i$ is dependent on the filter width of the running averaging or of the sum operator. This noise signal influences the correction images $D_{i+1}$ and therefore can lead to undesired noise structures in the resulting image in the case of a number of defective detector channels. A high filter width is required as a result. The intensity of a line artifact varies, however, so that a limitation of the filter width of the running averaging or of the sum operator is required.

The summation of the HU values in $G^1_i$ in the tangent direction $D^1_i$ or in $G^2_i$ in the tangent direction $D^2_i$ represents an additional measure for suppressing noise. This corresponds to the calculation of the radon values in these tangent directions. This operation of the image processing is referred to as HUG transformation. On the basis of a threshold criterion, a noise signal can be principally differentiated from artifact structures and can be eliminated. This threshold must be suitably selected, however, so that low-contrast lines in $G^1_i$ and $G^2_i$, that are actually a part of the diagnostically relevant image context, are not erroneously eliminated.

DESCRIPTION OF THE PREFERRED EMBODIMENTS

Figure 1:
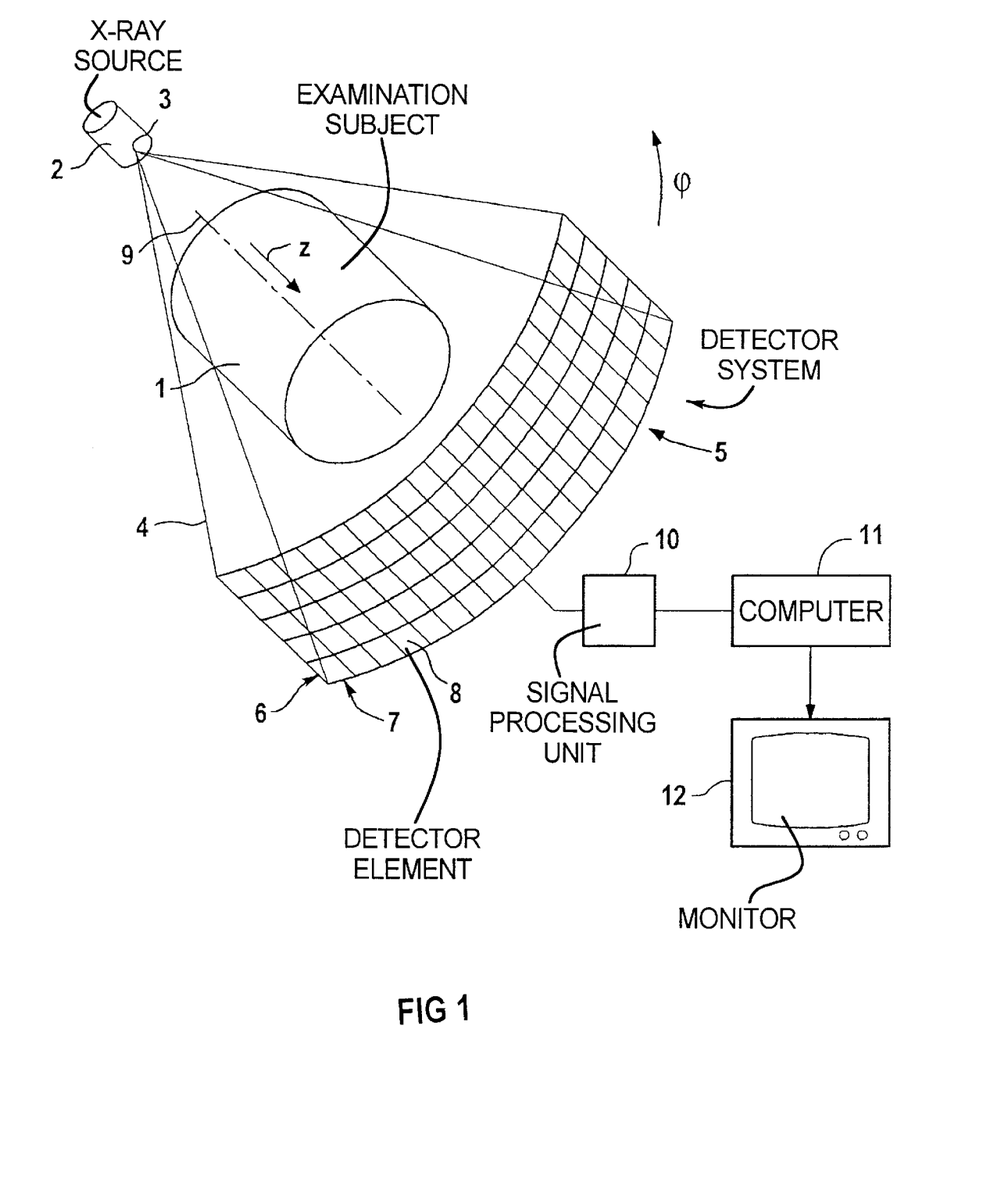
FIG. 1 schematically illustrates the basic components of an X-ray computed tomography apparatus, constructed and operating in accordance with the invention.

FIG. 1 shows a CT device, which is provided for scanning an examination subject 1, having an X-ray source 2, such as an X-ray tube, with a focus 3 from which a pyramid-shaped X-ray bundle 4 is emitted, which is gated by a radiation diaphragm (not shown) and which penetrates the examination subject 1, for example a patient, and strikes a detector system 5. The detector system 5 is an array of parallel rows 6 and parallel columns 7 of detector elements 8. The X-ray source 2 and the detector system 5 form a measuring system, which can be rotated in a direction 6 around a system axis 9 and which can be displaced along the system axis 9 relative to the examination subject 1, so that the examination subject is irradiated from different projection angles and in different z-positions along the system axis 9. A signal processing unit 10 forms measurement values from the output signals of the detector elements 8 of the detector system 5. These measurement values are supplied to a computer 11, which calculates an image of the examination subject 1, which is reproduced at the monitor 12.

Figure 2:
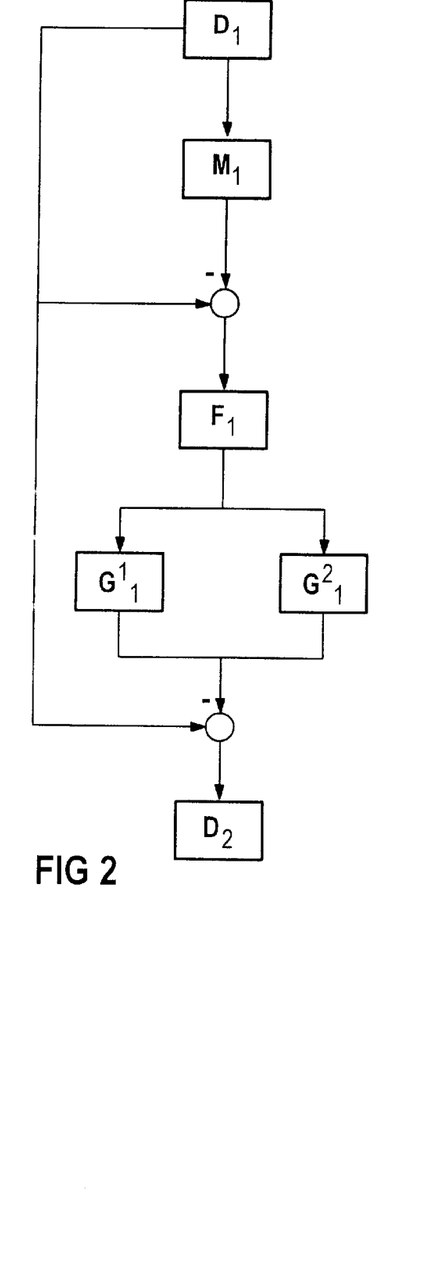
FIG. 2 is a flow chart for describing an exemplary embodiment of the inventive method for reducing line artifacts.

The flow chart as shown in FIG. 2 illustrates the inventive method for reducing line artifacts given a defective detector channel. The artifacts caused by the defective detector channel are situated on a circle $K_1$. They are already corrected in a known manner in the CT image $D_1$, so that the circle $K_1$ is no longer visible therein. As an undesired side effect of this correction, line artifacts, as tangents to the circle $K_1$, appear in the CT image $D_1$. A median filtering orthogonal to the straight line, which extends through the respective picture element of the CT image $D_1$ and the center of the circle $K_1$, produces the image $M_1$ from the CT image $D_1$. A difference value image $F_1$ is produced by subtracting the image $M_1$ from the CT image $D_1$. Two resulting images $G^1_1$ and $G^2_1$ are derived from the difference value image $F_1$ as a result of a further filter operation. The filtering ensues on the basis of each picture element of $F_1$ situated outside of the circle $K_1$ in the direction of the tangents to $K_1$. The filtering is carried out along the tangent $t^1$ for the resulting image $G^1_1$ and is carried out along the tangent $t^2_1$ for the resulting image $G^2_1$. The line artifacts that are present in the error image $F_1$ thus are emphasized in the resulting images $G^1_1$ and $G^2_1$. The two resulting images $G^1_1$ and $G^2_1$ are subsequently subtracted from the original CT image $D_1$, and the CT image $D_2$ is obtained, which no longer contains any visible line artifacts.

Figure 3:
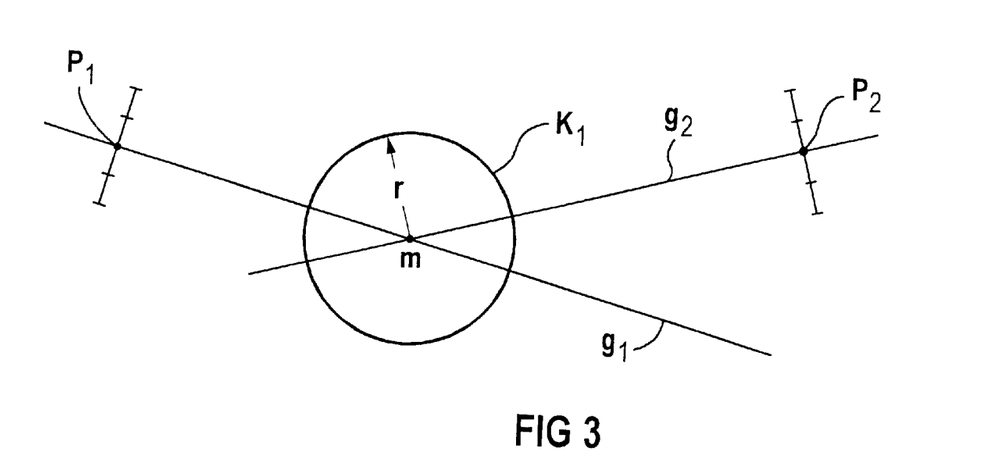
FIG. 3 is a schematic representation of a median filtering in the inventive method.

FIG. 3 schematically shows an exemplary median filtering. Shown are the circle $K_1$ with the center m and radius r, the two picture elements $P_1$ and $P_2$, as well as the straight lines $g_1$ and $g_2$, respectively through $P_1$ or $P_2$ and the center m. Furthermore, the positions of adjacent picture elements for $P_1$ and $P_2$ is indicated, which are situated on an orthogonal straight line with regard to $g_1$ and $g_2$, respectively. Given the median filtering, a mean value is formed in the example from $P_1$ and the four illustrated adjacent picture elements, and from $P_2$ and the four corresponding adjacent picture elements, and is utilized as a new image value of $P_1$ and $P_2$, respectively.

Figure 4:
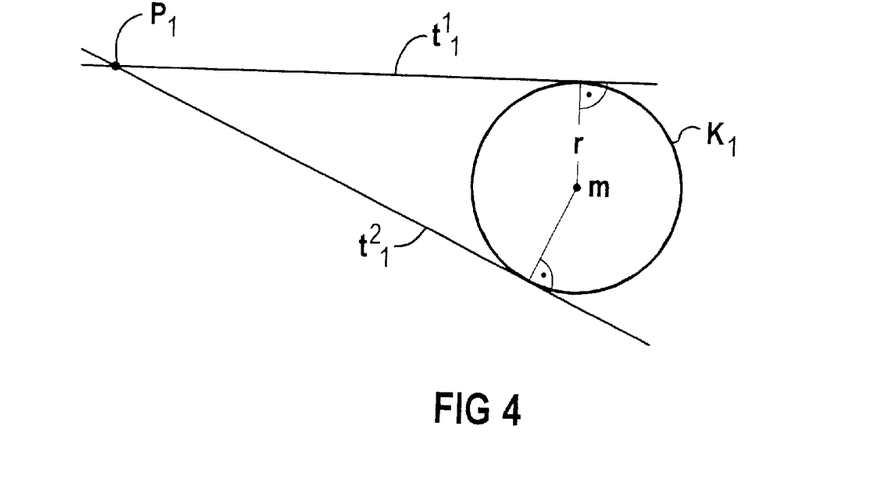
FIG. 4 is a schematic representation of a running averaging in the inventive method.
Figure 5:
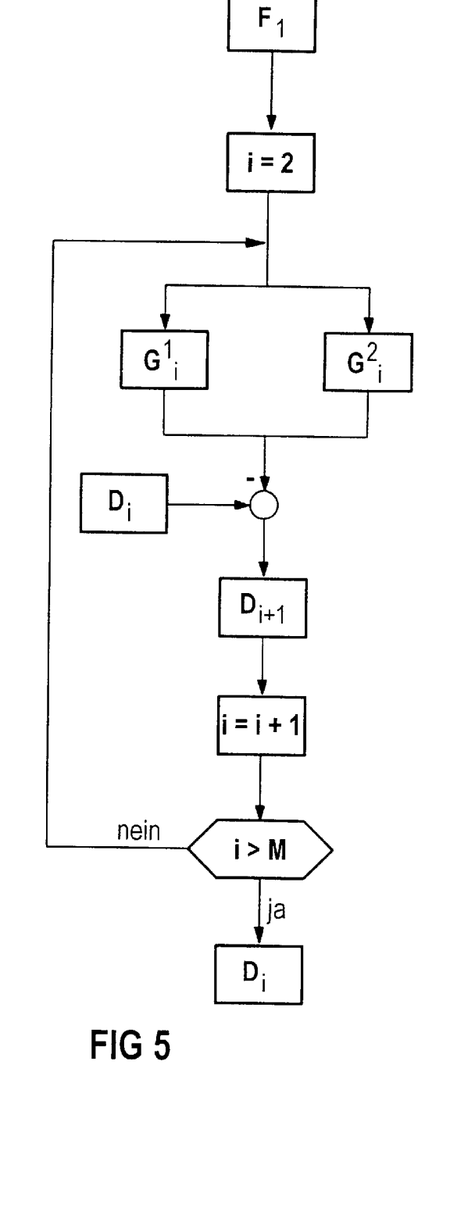
FIG. 5 illustrates the extension of the method according to FIG. 2 given more than one defective detector channel.

FIG. 4 schematically shows pixel-dependent averages. The directions of the averages in the picture element $P_1$ are fixed by the tangents $t^1_1$ and $t^2_1$ to the circle $K_1$ having the radius r and the center m, this circle $K_1$ being defined by the defective detector channel FIG. 5 shows the expansion of the method of FIG. 2 to more than one defective detector channel. On the basis of the difference value image $F_1$, the two result images $G^1_i$ and $G^2_i$ are produced by filtering the picture elements of $F_1$ in the direction of the tangents $t^1_i$ and $t^2_1$ to the circle $K_i$ extending through the respective picture element. The filtering along the tangent $t^1_i$ leads to the resulting image $G^1_i$ and the filtering along the tangent $t^2_i$ leads to the resulting image $G^2_i$. The resulting images $G^1_i$ and $G^2_i$ are subtracted from the image $D_i$. The image $D_{i+1}$ arises. The index i is increased by 1 and the method is repeated until i>M. The last-determined image $D_i$ with i=M+1 is displayed as the CT image at the monitor.

Figure 6:
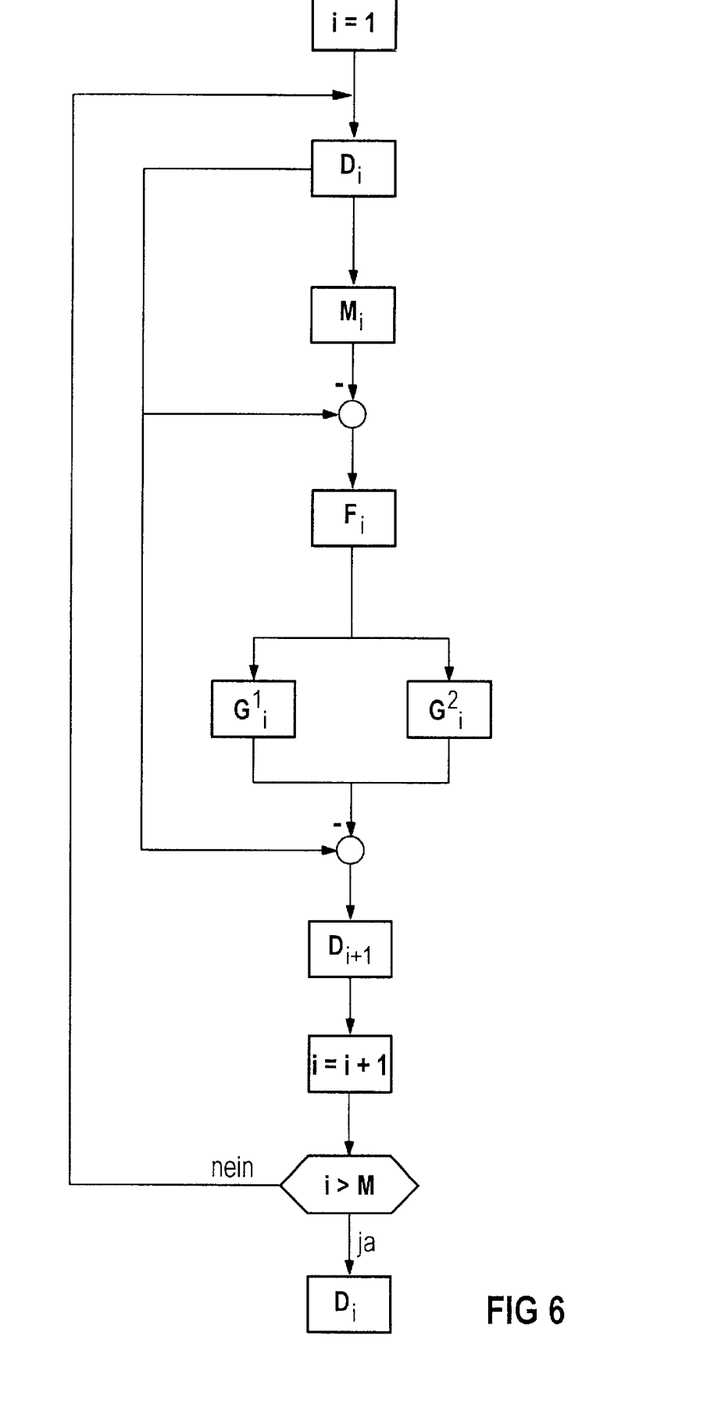
FIG. 6 is a flow chart for the inventive method for reducing line artifacts with an exact calculation of error images.

In contrast to FIG. 5, the error image $F_i$ is exactly calculated for each defective detector channel in the method shown in FIG. 6. For this purpose, the median filtering is carried out for each picture element of $D_i$ situated outside of the circle $K_i$ in the direction of the tangents to the circle $K_1$ extending through the respective picture element. The number of error images to be calculated in this method therefore corresponds to the number of defective detector channels. In addition to the error image, the two resulting images $G^1_i$ and $G^2_i$ therefore are produced anew for each detector channel. The remaining method steps corresponds to the method steps described in FIGS. 2 and 5. This method, which is more complicated compared to that of FIG. 2 or FIG. 6, also is repeated until all defective detector channels are processed.

Figure 7:
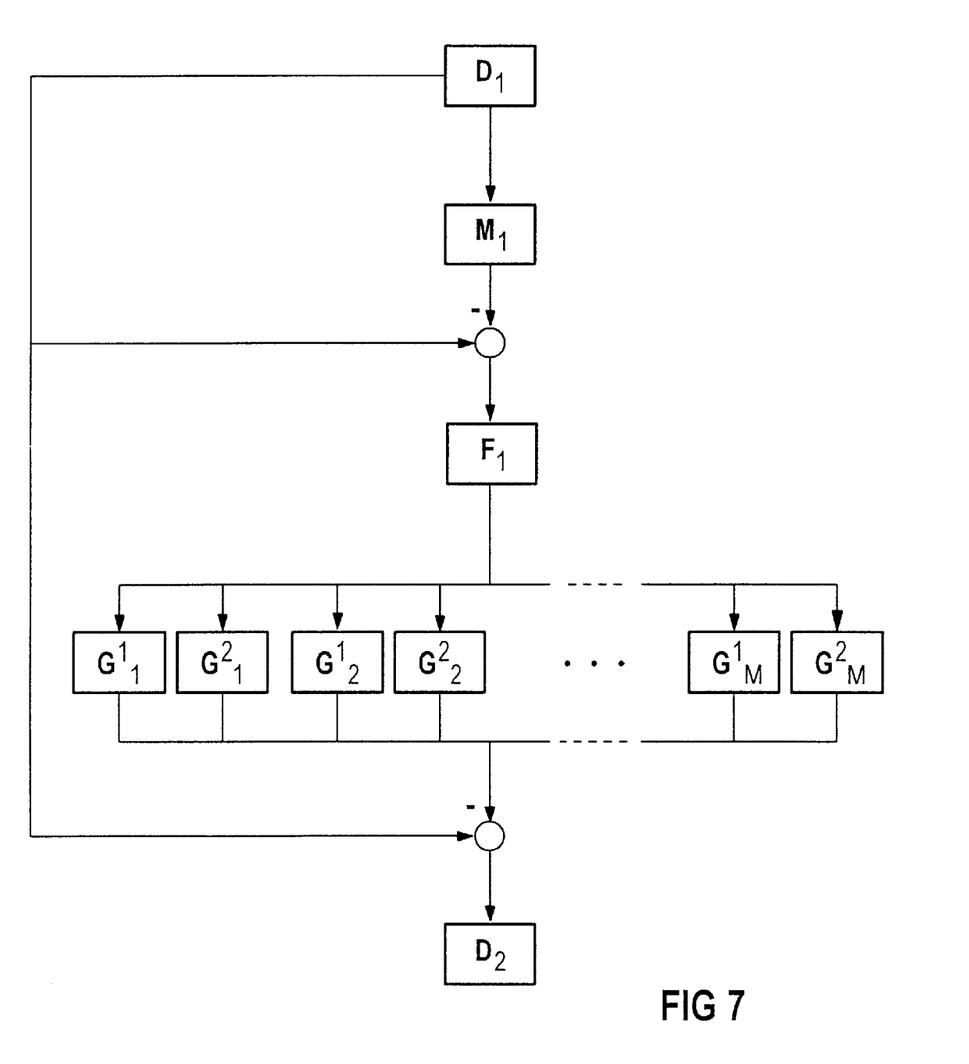
FIG. 7 is a flow chart for the inventive method for reducing line artifacts with some of the data processing taking place in parallel.

FIG. 7 shows an exemplary method embodiment, wherein the resulting images $G^1_i$ and $G^2_i$ are not sequentially calculated as in the previously described embodiments for a number of defective detector channels, but instead the result images $G^1_i$ and $G^2_i$, $1 \leq i \leq M$, are calculated in parallel for the multiple defective detector channels. On the basis of the CT image $D_1$, the image $M_1$ also initially arises as a result of a median filtering, and this image $M_1$ is subtracted from $D_1$ for calculating the image $F_1$. The resulting images $G^1_i$ and $G^2_i$, $1 \leq i \leq M$, which are determined in parallel on the basis of $F_1$, also are subtracted from the CT image $D_1$ for producing the CT image $D_2$. Assuming the availability of a very powerful computer, this method has a time advantage for the correction of the line artifacts in the CT images. Since the use of filter for calculating a resulting image has an effect on the adjacent resulting images, the defective detector elements should have a minimum spacing of ten channels from each other in order to be able to reconstruct a CT image that is free of line artifacts.

The efficacy of the method is demonstrated below on the basis of actual image data, acquired with a SIEMENS SOMATOM PLUS 4 VOLUME ZOOM CT device.

Figure 8:
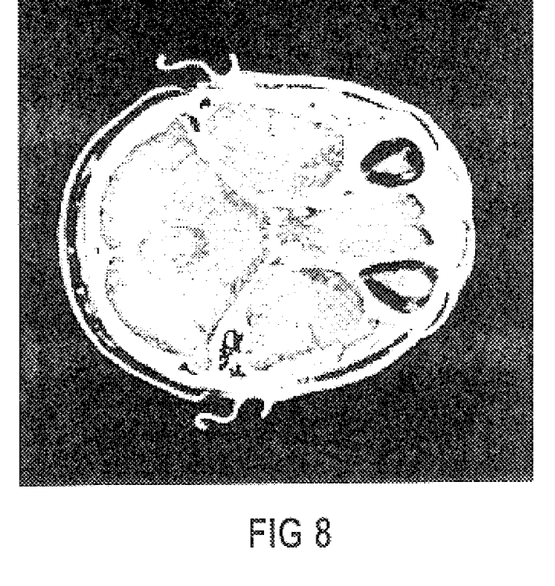
FIG. 8 shows a reference CT image of the skull base.
Figure 9:
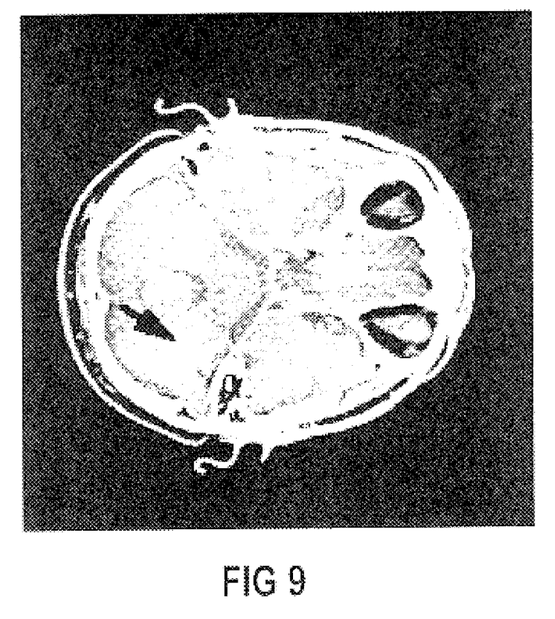
FIG. 9 shows a CT image having high-contrast line artifacts.
Figure 10:
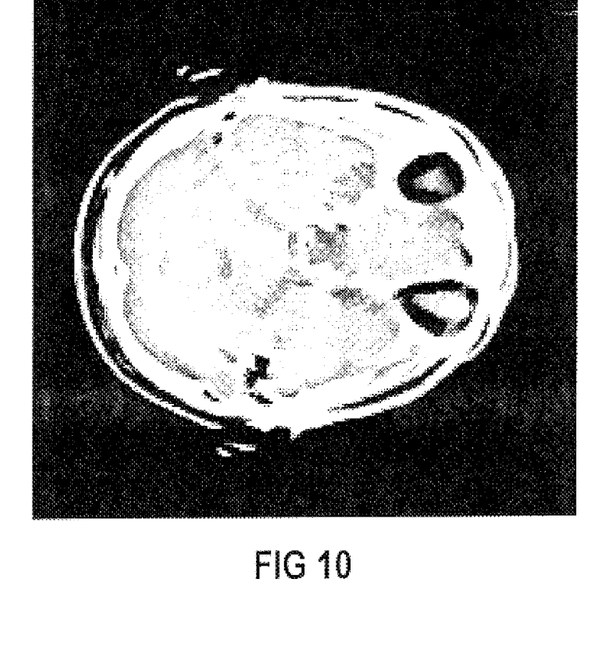
FIG. 10 shows the CT image of FIG. 9 after median filtering in accordance with the inventive method.
Figure 11:
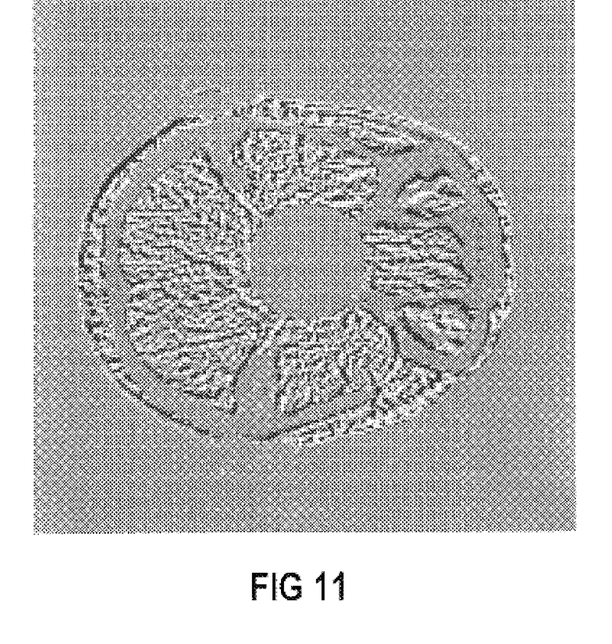
FIG. 11 shows the difference value image formed from the respective images of FIG. 10 and FIG. 9 in accordance with the inventive method.
Figure 12:
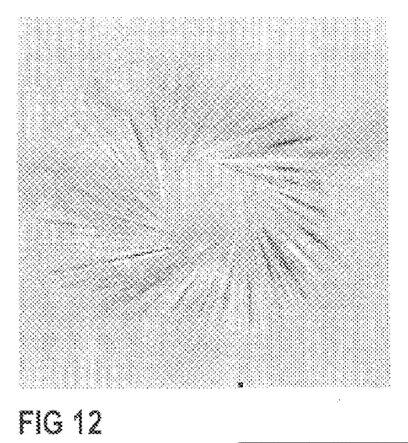
FIG. 12 shows the resulting image $G^1_1$ formed by a running averaging of the difference value image of FIG. 11 in accordance with the inventive method.
Figure 13:
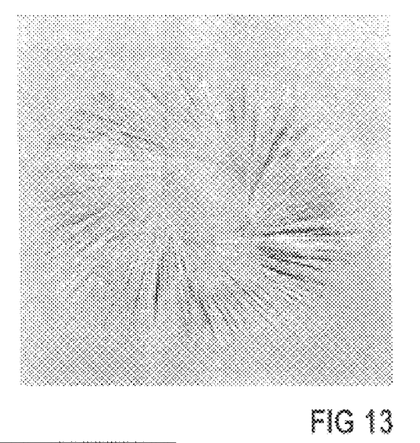
FIG. 13 shows the resulting image $G^2_1$ formed by a running averaging of the difference value image of FIG. 11 in accordance with the inventive method.
Figure 14:
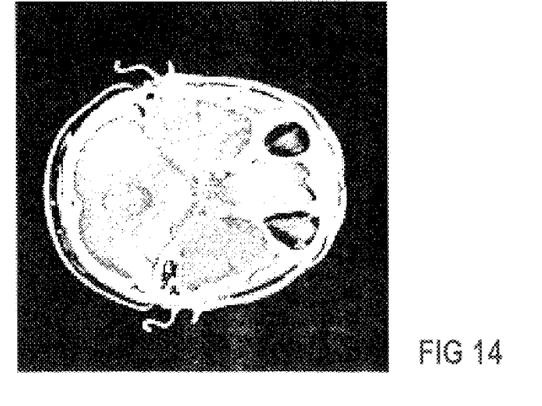
FIG. 14 shows the correction image D2 obtained in accordance with the inventive method.

As a reference CT image, FIG. 8 shows image data of the skull basis given a scan carried out in a 4×1 slice modus, axial scan operation. The measuring data of a detector row are evaluated, whereby a predefined individual channel does not supply measurement values. A linear interpolation eliminates the circle artifacts arising as a result of the "defective" channel. As shown in FIG. 9, the result is the CT image, which serves as an initial CT image $D_1$ for the inventive method and which has a high-contrast line artifact at the location marked by the arrow, for example. The method as shown in FIG. 2 is used for eliminating the line artifacts. FIG. 10 shows the median-filtered input image $M_1$. Given the subtraction of $M_1$ from the original CT image $D_1$, the difference value image $F_1$ essentially showing the line artifacts and image noise results as shown in FIG. 11. A running averaging in the direction of the tangents of the circle caused by the defective detector channel subsequently results for each pixel of the difference value image $F_1$. Since—proceeding from each pixel of the difference value image $F_1$—there are two possible tangents to the circle, two resulting images $G^1_1$ and $G^2_1$ are produced. These are shown in the FIGS. 12 and 13. Ideally, the image noise is mainly suppressed in these images. When the two resulting images $G^1_1$ and $G^2_1$ are subtracted from the original CT image $D_1$ as shown in FIG. 9, the correction image $D_2$ as shown in FIG. 14 results. As can be seen from $D_2$, the line artifacts have been effectively suppressed without increasing the noise contribution.

For the practical realization of a method according to the invention, only the corrected images are displayed at the monitor. The method process therefore proceeds essentially on the basis of computer-internal "image data", which are not reconstructed as "images" at the monitor.

In the described exemplary embodiments, CT devices of the third generation are shown, i.e., the X-ray source and the detector rotate together around the system axis during the image generation. The invention also can be used with CT devices of the fourth generation, wherein only the X-ray source rotates and cooperates with a stationary detector ring.

The described exemplary embodiments relate to the medical application of inventive CT devices. The invention can also be applied outside of the medical field baggage inspection or material testing, for example.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for reducing line artifacts in a CT image $D_1$, acquired by scanning an examination subject by rotating at least a focus of an X-ray source around the examination subject and detecting radiation, attenuated by said examination subject, with a detector system which has a plurality of proper detector channels and at least one defective detector channel, and wherein said CT image $D_1$ is subjected to an interpolated filtering for preventing or correcting faulty values of picture elements represented on a circle $K_1$, said faulty values being caused by the defective detector channel, comprising the steps of:

(a) subjecting picture elements of the CT image $D_1$ to a median filtering, orthogonal to a straight line extending through the respective picture element and a center of the circle $K_1$, for producing an image $M_1$;

(b) forming a difference value image $F_1 = D_1 - M_1$ by subtracting the image $M_1$ from the CT image $D_1$;

(c) producing two resulting images $G^1_1$ and $G^2_1$ by filtering picture elements of the difference value image $F_1$ in respective directions of tangents $t^1_1$ and $t^2_1$ to the circle $K_1$ extending through the respective picture element, whereby the filtering is conducted along $t^1_1$ for the resulting image $G^1_1$ and is conducted along $t^2_1$ for the resulting image $G^2_1$; and (d) forming a correction image $D_2 = D_1 - G^1_1 - G^2_1$ by subtracting the resulting images $G^1_1$ and $G^2_1$ from $D_1$.

2. A method for reducing line artifacts in a correction image $D_2$ as claimed in claim 1, wherein the number of the defective detector channels equals M (M>1) and wherein i is a running index with i=2 ... M, further comprising:

(e) producing said two resulting images $G^1_i$ and $G^2_i$ by filtering picture elements of the difference value image $F_1$ in respective directions of tangents $t^1_i$ and $t^2_i$ to the circle $K_1$ extending through the respective picture element, whereby the filtering is conducted along $t^1_i$ for the resulting image $G^1_i$ and is conducted along $t^2_i$ for the resulting image $G^2_i$;

(f) forming a correction image $D_{i+1} = D_i - G^1_i - G^2_i$ by subtracting the resulting images $G^1_i$ and $G^2_i$ from $D_i$.

(g) increasing the index i by one, and repeating steps (e) to (g) until i>M.

3. A method as claimed in claim 1 comprising adjusting a width of said median filtering.

4. A method as claimed in claim 1 wherein the step of filtering said picture elements to produce said resulting images $G^1_1$ and $G^2_1$ comprises conducting a running averaging along the respective tangents $t^1_1$ and $t^2_1$.

5. A method as claimed in claim 1 wherein the step of filtering said picture elements to produce the resulting images $G^1_1$ and $G^2_1$ comprises employing a sum operator along said tangents $t^1_1$ and $t^2_1$.

6. A method as claimed in claim 1 wherein the step of filtering said picture elements to produce the resulting images $G^1_1$ and $G^2_1$ comprises conducting a running averaging and employing a sum operator along said tangents $t^1_1$ and $t^2_1$.

7. A method as claimed in claim 1 comprising limiting values of the picture elements of the CT image $D_1$ to a range 1,000 $HU(H_2O) \pm \Delta$.

8. A method for reducing line artifacts in a CT image $D_1$, acquired by scanning an examination subject by rotating at least a focus of an X-ray source around the examination subject and detecting radiation, attenuated by said examination subject, with a detector system which has a plurality of proper detector channels and at least one defective detector channel, and wherein said CT image $D_1$ is subjected to an interpolated filtering for preventing or correcting faulty values of picture elements represented on a circle $K_1$, said faulty values being caused by an $i^{th}$ defective detector channel, said method comprising the steps of:
  (a) subjecting picture elements of the CT image $D_1$ to a median filtering, orthogonal to a straight line extending through the respective picture element and a center of the circle $K_i$, for producing an image $M_1$;
  (b) forming a difference value image $F_1 = D_1 - M_1$ by subtracting the image $M_1$ from the CT image $D_1$;
  (c) producing two resulting images $G^1_i$ and $G^2_i$ by filtering picture elements of the difference value image $F_1$ in respective directions of tangents $t^1_i$ and $t^2_i$ to the circle $K_i$ extending through the respective picture element, whereby the filtering is conducted along $t^1_i$ i for the resulting image $G^1_i$ and is conducted along $t^2_i$ for the resulting image $G^2_i$; and
  (d) forming a correction image $D_2 = D_1 - G^1_i - G^2_i$, $1 \leq i \leq M$, by subtracting the resulting images $G^1_i$ and $G^2_i$ from $D_1$.

9. A method as claimed in claim 8 comprising adjusting a width of said median filtering.

10. A method as claimed in claim 8 wherein the step of filtering said picture elements to produce said resulting images $G^1_i$ and $G^2_i$ comprises conducting a running averaging along the respective tangents $t^1_i$ and $t^2_i$.

11. A method as claimed in claim 8 wherein the step of filtering said picture elements to produce the resulting images $G^1_i$ and $G^2_i$ comprises employing a sum operator along said tangents $t^1_i$ and $t^2_i$.

12. A method as claimed in claim 8 wherein the step of filtering said picture elements to produce the resulting images $G^1_i$ and $G^2_i$ comprises conducting a running averaging and employing a sum operator along said tangents $t^1_i$ and $t^2_i$.

13. A method as claimed in claim 8 comprising limiting values of the picture elements of the CT image $D_1$ to a range 1,000 $HU(H_2O) \pm \Delta$.

14. A computed tomography apparatus comprising:
  an X-ray source for scanning an examination subject by rotating at least a focus of said X-ray source around the examination subject;
  a detector system for detecting radiation, attenuated by said examination subject, which has a plurality of proper detector channels and at least one defective detector channel said detector system emitting electrical signals representing data comprising a CT image $D_1$; and
  a computer connected to said detector system wherein said CT image $D_1$ is subjected to an interpolated filtering for preventing or correcting faulty values of picture elements represented on a circle $K_1$, said faulty values being caused by the defective detector channel, for reducing line artifacts in said CT image $D_1$, said computer subjecting picture elements of the CT image $D_1$ to a median filtering, orthogonal to a straight line extending through the respective picture element and a center of the circle $K_1$, for producing an image $M_1$, and forming a difference value image $F_1 = D_1 - M_1$ by subtracting the image $M_1$ from the CT image $D_1$, and producing two resulting images $G^1_1$ and $G^2_1$ by filtering picture elements of the difference value image $F_1$ in respective directions of tangents $t^1_1$ and $t^2_1$ to the circle $K_1$ extending through the respective picture element, whereby the filtering is conducted along $t^1_1$ for the resulting image $G^1_1$ and is conducted along $t^2_1$ for the resulting image $G^2_1$, and forming a correction image $D_2 = D_1 - G^1_1 - G^2_1$ by subtracting the resulting images $G^1_1$ and $G^2_1$ from $D_1$.

15. A computed tomography apparatus as claimed in claim 14, wherein the number of the defective detector channels equals M (M>1) and wherein i is a running index with i=2 . . . M, wherein said computer produces said two result images $G^1_i$ and $G^2_i$ by filtering picture elements of the difference value image $F_1$ in respective directions of tangents $t^1_i$ and $t^2_i$ to the circle $K_1$ extending through the respective picture element, said computer conducting the filtering along $t^1_i$ for the resulting image $G^1_i$ and along $t^2_i$ for the resulting image $G^2_i$.

16. A computed tomography apparatus as claimed in claim 14 wherein said computer adjusts a width of said median filtering.

17. A computed tomography apparatus as claimed in claim 14 wherein said computer filters said picture elements to produce said resulting images $G^1_1$ and $G^2_1$ by conducting a running averaging along the respective tangents $t^1_1$ and $t^2_2$.

18. A computed tomography apparatus as claimed in claim 14 wherein said computer filters said picture elements to produce the resulting images $G^1_1$ and $G^2_1$ by employing a sum operator along said tangents $t^1_1$ and $t^2_1$.

19. A computed tomography apparatus as claimed in claim 14 wherein said computer filters said picture elements to produce the resulting images $G^1_1$ and $G^2_1$ by conducting a running averaging and employing a sum operator along said tangents $t^1_1$ and $t^2_1$.

20. A computed tomography apparatus as claimed in claim 14 wherein said computer limits values of the picture elements of the CT image $D_1$ to a range 1,000 $HU(H_2O) \pm \Delta$.

21. A computed tomography apparatus comprising:
  an X-ray source for scanning an examination subject by rotating at least a focus of said X-ray source around the examination subject;
  a detector system for detecting radiation, attenuated by said examination subject, which has a plurality of proper detector channels and at least one defective detector channel said detector system emitting electrical signals representing data comprising a CT image $D_1$; and
  a computer connected to said detector system wherein said CT image $D_1$ is subjected to an interpolated filtering for preventing or correcting faulty values of picture elements represented on a circle $K_1$, said faulty values being caused by an $i^{th}$ defective detector channel, for reducing line artifacts in said CT image, said computer subjecting picture elements of the CT image $D_1$ to a median filtering, orthogonal to a straight line extending through the respective picture element and a center of the circle $K_i$, for producing an image $M_1$, and forming a difference value image $F_1 = D_1 - M_1$ by subtracting the image $M_1$ from the CT image $D_1$, and producing two resulting images $G^1_i$ and $G^2_i$ by filtering picture elements of the difference value image $F_1$ in respective directions of tangents $t^1_i$ and $t^2_i$ to the circle $K_i$ extending through the respective picture element, whereby the filtering is conducted along $t^1_i$ for the resulting image $G^1_i$ and is conducted along $t^2_i$ for the resulting image $G^2_i$ and forming a correction image $D_2=D_1-G^1_i-G^2_i$, $1 \leq i \leq M$, by subtracting the resulting images $G^1_i$ and $G^2_i$ from $D_1$.

22. A computed tomography apparatus as claimed in claim 21 wherein said computer adjusts a width of said median filtering.

23. A computed tomography apparatus as claimed in claim 21 said computer filters said picture elements to produce said resulting images $G^1_i$ and $G^2_i$ comprises conducting a running averaging along the respective tangents $t^1_i$ and $t^2_i$.

24. A computed tomography apparatus as claimed in claim 21 wherein said computer filters said picture elements to produce the resulting images $G^1_i$ and $G^2_i$ comprises employing a sum operator along said tangents $t^1_i$ and $t^2_i$.

25. A computed tomography apparatus as claimed in claim 21 wherein said computer filters said picture elements to produce the resulting images $G^1_i$ and $G^2_i$ by conducting a running averaging and employing a sum operator along said tangents $t^1_i$ and $t^2_i$.

26. A computed tomography apparatus as claimed in claim 21 wherein said computer limits values of the picture elements of the CT image $D_1$ to a range 1,000 $HU(H_2O) \pm \Delta$.

27. A method for reducing line artifacts in a CT image $D_1$, acquired by scanning an examination subject by rotating at least a focus of an X-ray source around the examination subject and detecting radiation, attenuated by said examination subject, with a detector system which has a plurality of proper detector channels and at least one defective detector channel, and wherein said CT image $D_1$ is subjected to an interpolated filtering for preventing or correcting faulty values of picture elements represented on a circle $K_1$, said faulty values being caused by the defective detector channel, comprising the steps of:

(a) subjecting picture elements of the CT image $D_1$ to a median filtering, orthogonal to tangents to said circle $K_1$ and extending through the respective picture element, for producing an image $M_1$;

(b) forming a difference value image $F_1=D_1-M_1$ by subtracting the image $M_1$ from the CT image $D_1$;

(c) producing two resulting images $G^1_1$ and $G^2_1$ by filtering picture elements of the difference value image $F_1$ in respective directions of tangents $t^1_1$ and $t^2_1$ to the circle $K_1$ extending through the respective picture element, whereby the filtering is conducted along $t^1_1$ for the resulting image $G^1_1$ and is conducted along $t^2_1$ for the resulting image $G^2_1$; and (d) forming a correction image $D_2=D_1-G^1_1-G^2_1$ by subtracting the resulting images $G^1_1$ and $G^2_1$ from $D_1$.

28. A method for reducing line artifacts in a correction image $D_2$ as claimed in claim 27, wherein the number of the defective detector channels equals M (M>1) and wherein i is a running index with i=2 . . . M, further comprising:

(e) subjecting picture elements of the CT image $D_1$ to a median filtering, orthogonal to a straight line extending through the respective picture element and a center of the circle $K_i$, for producing an image $M_1$;

(f) forming a difference value image $F_i=D_i-M_i$ by subtracting the image $M_1$ from the CT image $D_i$;

(g) producing two resulting images $G^1_i$ and $G^2_i$ by filtering picture elements of the difference value image $F_1$ in respective directions of tangents $t^1_i$ and $t^2_i$ to the circle $K_i$ extending through the respective picture element, whereby the filtering is conducted along $t^1_i$ for the resulting image $G^1_i$ and is conducted along $t^2_i$ for the resulting image $G^2_i$; and (h) forming a correction image $D_{i+1}=D_i-G^1_i-G^2_i$, $1 \leq i \leq M$, by subtracting the resulting images $G^1_i$ and $G^2_i$ from $D_i$.

29. A method as claimed in claim 27 comprising adjusting a width of said median filtering.

30. A method as claimed in claim 27 wherein the step of filtering said picture elements to produce said resulting images $G^1_1$ and $G^2_1$ comprises conducting a running averaging along the respective tangents $t^1_1$ and $t^2_1$.

31. A method as claimed in claim 27, wherein the step of filtering said picture elements to produce the resulting images $G^1_1$ and $G^2_1$ comprises employing a sum operator along said tangents $t^1_1$ and $t^2_1$.

32. A method as claimed in claim 27 wherein the step of filtering said picture elements to produce the resulting images $G^1_1$ and $G^2_1$ comprises conducting a running averaging and employing a sum operator along said tangents $t^1_1$ and $t^2_1$.

33. A method as claimed in claim 27 comprising limiting values of the picture elements of the CT image $D_1$ to a range 1,000 $HU(H_2O) \pm \Delta$.

34. A computed tomography apparatus comprising:

an X-ray source for scanning an examination subject by rotating at least a focus of said X-ray source around the examination subject;

a detector system for detecting radiation, attenuated by said examination subject, which has a plurality of proper detector channels and at least one defective detector channel said detector system emitting electrical signals representing data comprising a CT image $D_1$; and a computer connected to said detector system wherein said CT image $D_1$ is subjected to an interpolated filtering for preventing or correcting faulty values of picture elements represented on a circle $K_1$, said faulty values being caused by the defective detector channel, for reducing line artifacts in said CT image $D_1$, said computer subjecting picture elements of the CT image $D_1$ to a median filtering, orthogonal to tangents to said circle $K_1$ extending through the respective picture element, for producing an image $M_1$ and forming a difference value image $F_1=D_1-M_1$ by subtracting the image $M_1$ from the CT image $D_1$, and producing two resulting images $G^1_1$ and $G^2_1$ by filtering picture elements of the difference value image $F_1$ in respective directions of tangents $t^1_1$ and $t^2_1$ to the circle $K_1$ extending through the respective picture element, whereby the filtering is conducted along $t^1_1$ for the resulting image $G^1_1$ and is conducted along $t^2_1$ for the resulting image $G^2_1$, and forming a correction image $D_2=D_1-G^1_1-G^2_1$ by subtracting the resulting images $G^1_1$ and $G^2_1$ from $D_1$.

35. A computed tomography apparatus as claimed in claim 34, wherein the number of the defective detector channels equals M (M>1) and wherein i is a running index with i=2 . . . M, said computer subjecting picture elements of the CT image $D_1$ to a median filtering, orthogonal to a straight line extending through the respective picture element and a center of the circle $K_i$ for producing an image $M_1$ and forming a difference value image $F_i=D_i-M_i$ by subtracting the image $M_i$ from the CT image $D_i$, and producing two resulting images $G^1_i$ and $G^2_i$ by filtering picture elements of the difference value image $F_i$ in respective directions of tangents $t^1_i$ and $t^2_i$ to the circle $K_i$ extending through the respective picture element, whereby the filtering is conducted along $t^1_i$ for the resulting image $G^i_1$ and is conducted along $t^2_i$ for the resulting image $G^2_i$, and forming a correction image $D_{i+1}=D_i-G^1_i-G^2_i$ by subtracting the resulting images $G^1_i$ and $G^2_i$ from $D_i$.

36. A computed tomography apparatus as claimed in claim 34 wherein said computer adjusts a width of said median filtering.

37. A computed tomography apparatus as claimed in claim 34 wherein said computer filters said picture elements to produce said resulting images $G^1_1$ and $G^2_1$ by conducting a running averaging along the respective tangents $t^1_1$ and $t^2_2$.

38. A computed tomography apparatus as claimed in claim 34, wherein said computer filters said picture elements to produce the resulting images $G^1_1$ and $G^2_1$ by employing a sum operator along said tangents $t^1_1$ and $t^2_1$.

39. A computed tomography apparatus as claimed in claim 34 wherein said computer filters said picture elements to produce the resulting images $G^1_1$ and $G^2_1$ by conducting a running averaging and employing a sum operator along said tangents $t^1_1$ and $t^2_1$.

40. A computed tomography apparatus as claimed in claim 34 wherein said computer limits values of the picture elements of the CT image $D_1$ to a range $1{,}000\ HU(H_2O)\pm\Delta$.

* * * * *